United States Patent
Eross

[11] 3,953,060
[45] Apr. 27, 1976

[54] SLIP-PROOF COUPLING DEVICE
[75] Inventor: Bela Eross, Penn Hills Township, Allegheny County, Pa.
[73] Assignee: Instrumentation Industries, Inc., Pittsburgh, Pa.
[22] Filed: Sept. 20, 1971
[21] Appl. No.: 181,705

[52] U.S. Cl. ............................... 285/272; 285/305; 24/201 R
[51] Int. Cl.² ..................... F16L 27/08; F16L 37/00
[58] Field of Search ........... 24/201 R, 201 S, 230 R; 128/145, 145.5; 285/8, 272, 305, 319, DIG. 22, 114; 339/75; 61/12

[56] References Cited
UNITED STATES PATENTS

| 1,514,276 | 11/1924 | Whalen et al. | 285/272 X |
| 2,461,427 | 2/1949 | Kneebone | 285/114 X |
| 2,728,058 | 12/1955 | Phalen | 339/75 P |
| 3,038,469 | 6/1962 | Jacuzzi | 285/305 X |
| 3,262,721 | 7/1966 | Knight | 285/DIG. 22 |
| 3,461,877 | 8/1969 | Morch | 128/145 R X |
| 3,603,621 | 9/1971 | Parsons | 285/319 |
| 3,638,968 | 2/1972 | Barks | 285/8 |

FOREIGN PATENTS OR APPLICATIONS

| 962,644 | 6/1950 | France | 61/12 |
| 1,007,746 | 10/1965 | United Kingdom | 285/114 |

Primary Examiner—Robert L. Wolfe
Assistant Examiner—David H. Corbin
Attorney, Agent, or Firm—Buell, Blenko, and Ziesenheim

[57] ABSTRACT

The specification discloses a coupling device comprising a sleeve, forming an adapter for connecting tubing of different sizes, particularly tubing used in respiratory systems in hospitals. The sleeve has fixed thereto a pair of external diametrically disposed mushroom-like buttons by which an elastic tape with a series of holes secures a tubing to the sleeve and prevents accidental separation therefrom.

1 Claim, 6 Drawing Figures

U.S. Patent   April 27, 1976   3,953,060
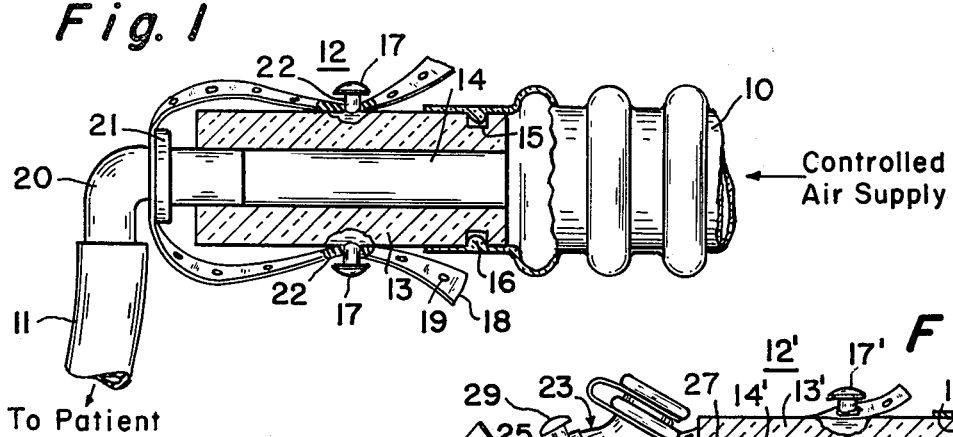
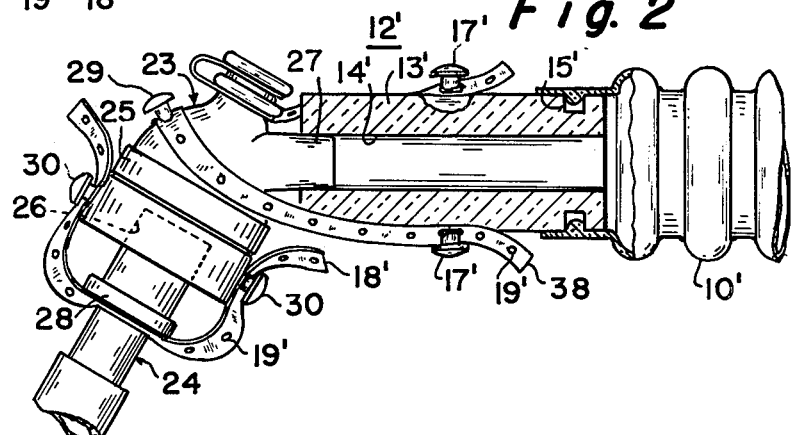
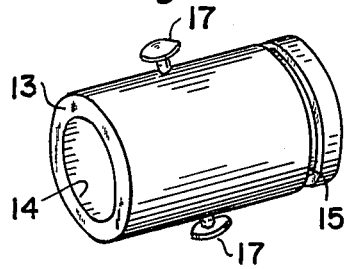
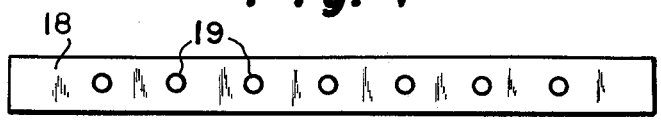
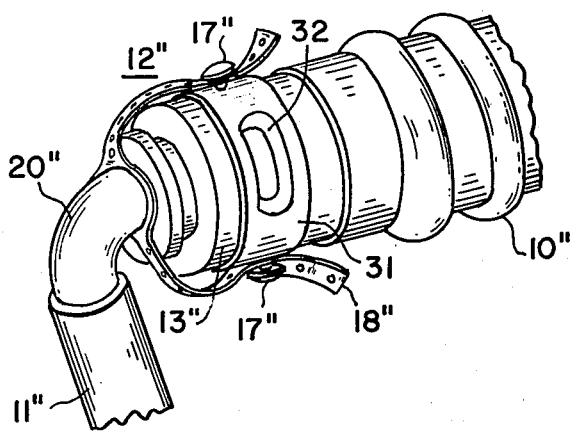
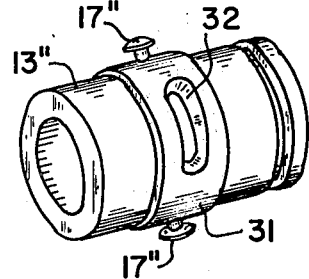
INVENTOR.
Bela Eross
BY
HIS ATTORNEYS

SLIP-PROOF COUPLING DEVICE

This invention relates to a coupling device for connecting sections of tubing of different sizes, particularly tubing in respiratory equipment used in hospitals, in such a manner as to prevent accidental separation of the tubing from the coupling device.

Respiratory equipment utilized in hospitals for the administration of assisted or controlled ventilation for patients, requires tubing of various sizes and types which must be quickly and readily connected. Since the well-being and perhaps even the life of the patient may depend on the assurance of assisted or controlled ventilation supply, it is also imperative that accidental separation of tubing at points of connection be avoided. By way of example, the point at which the endo-tracheal or tracheostomy tube is connected to a flexible tubing of the corrugated type conducting the supply of controlled or assisted ventilation from the nebulizer is commonly subject to accidental disconnection.

In the administration of spontaneous aerosol therapy via the endo-tracheal or tracheostomy tube, some provision is necessary to allow resistance free exhalation. This is customarily accomplished by connecting a T-fitting in the tubing supplying controlled ventilation to the patient, the one port of the T-fitting being open directly to atmosphere to allow the air exhaled by the patient to flow directly back to atmosphere in by-pass of the exhalation port of the nebulizer. The T-fitting necessitates the making of additional connections in the tubing. This requires additional time and, of course, increases the possible number of locations where accidental disconnections may occur.

In order to avoid the above-mentioned difficulties heretofore experienced, I propose to provide a coupling device in the form of a plastic sleeve which serves as an adapter between tubing of different sizes and which at the same time is provided with means for positively insuring against separation of a tubing from the coupling. Specifically, I propose to utilize an elastic strap with a series of holes of relatively small diameter which expand over mushroom-like buttons on the coupling device for positively holding the tubing and coupling together.

Moreover, in order to avoid the necessity of a separate T-fitting in spontaneous aerosol therapy tubing, I propose to provide a modified form of coupling device having in the coupling sleeve an exhalation port or slot to allow for resistance free exhalation.

Other advantages and improvements provided by the coupling device originated by me will become apparent in the following detailed description thereof, wherein:

FIG. 1 is a fragmental view, partly in section, showing one embodiment of my slip-proof coupling device, FIG. 2 is a fragmental view, also partly in section, illustrating a further application for the embodiment of coupling device shown in FIG. 1, FIG. 3 is a perspective view, at approximately full scale, of the sleeve portion of the embodiment of slip-proof coupling device shown in FIG. 1, FIG. 4 is a plan view, showing an elastic strap forming part of the embodiment of coupling device shown in FIG. 1, FIG. 5 is a fragmental perspective view, showing a modified embodiment of coupling device, having an exhalation port therein, and FIG. 6 is a perspective view, at approximately full scale, of the sleeve portion of the coupling device shown in FIG. 5.

Referring to FIG. 1 of the drawings, there is shown a flexible tube 10 through which flows a controlled air supply, an endo-tracheal or tracheostomy tube 11 by which the controlled air supply is introduced orally or by side incision in the throat to the trachea of the patient, and an embodiment of the coupling device 12, constituting the invention, connecting tubes 10 and 11.

Referring now additionally to FIGS. 3 and 4, the coupling device 12 comprises a cylindrical sleeve 13, of transparent plastic material, having a longitudinal through passage 14 of uniform circular cross-section. Externally, the sleeve 13 has a circumferential locking groove 15 adjacent one end, in which an internal sealing rib 16 adjacent the end of the flexible tube 10 is adapted to seat when the end of the tube 10 is telescoped over the end of the sleeve 13. Integrally formed on or attached to the external surface of the sleeve 13 substantially mid-way between the ends thereof are a pair of mushroom-like buttons 17. Buttons 17 are disposed preferably in diametrical relation to each other, as shown.

Also forming a part of the coupling device 12 is a strap 18 of elastic material, such as natural or synthetic rubber. Strap 18 has a series of substantially uniformly spaced holes 19 of relatively small diameter. The purpose and manner of application of strap 18 will be explained later.

The diameter of the through passage 14 is so chosen as to provide a seat at the end thereof for telescopically receiving in sealed relation the slightly tapered sleeve-like end of an elbow-fitting 20 of standard dimensions by which the endo-tracheal tube 11 is connected to the coupling. The elbow-fitting 20 has a collar or flange 21 which is utilized in the manner to be described hereinafter.

It will be apparent that the coupling device 12 serves as an adapter for coupling two tubes of different diameter, namely, the relatively large diameter tube 10 and the relatively small diameter elbow-fitting 20. The connection between the sealing rib 16 of flexible tube 10 and the groove 15 of the coupling device is such as to provide a sealed joint. Also, by reason of the force required to be manually exerted to expand the tubular end of the tube 10 to effect removal of the tube from the coupling device 12, accidental and unintentional separation of the tube 10 from the coupling 12 is relatively unlikely to occur.

Insofar as the telescoping joint between the elbow fitting 20 and the end of the passage 14 in the sleeve 13 is concerned, however, repeated twisting and turning forces encountered under service conditions are likely to cause separation of the fitting 20 from the coupling device 12 except for the provision of the strap 18, the manner of installation of which will now be described.

Before inserting the end of the elbow-fitting 20 in the endo-tracheal tube 11 to the patient, one of the more-centrally located holes 19 in the strap is expanded over the elbow-fitting. The elastic material of which the strap 18 is made stretches within the elastic limit thereof to accomodate the larger diameter of the elbow-fitting 20 relative to the diameter of the holes 19 in the strap 18. Strap 18 is shifted on the elbow-fitting to contact one side of the collar 21 on the fitting 20. The tube 11 is then telescopically slipped over the end of the elbow-fitting 20 and the fitting installed in the end of passage 14 of the coupling 12.

With the elbow-fitting 20 and the coupling 12 assembled as just described, one end of the strap 18 is stretched taut and while in such taut condition, a suitably located hole 19 in the strap is expanded over one of the buttons 17, the head of which is relatively larger in diameter than that of the hole 19. The diameter of the hole in the strap contracts after passing the head of the button 17 and conforms to that of the short stem 22 of the button. In a similar manner, the opposite end of the strap is now stretched taut and a conveniently located hole 19 in that portion of the strap expanded over the diametrically oppositely located button 17 and locked thereon.

It will now be seen that with the strap 18 installed as just described, the tension in the tautly stretched strap 18 exerts a force which safely holds the elbow-fitting 20 in the coupling device 12 against accidental separation.

The coupling device 12 is preferably installed before intubation of the endo-tracheal tube 11, that is prior to insertion of the tube into the throat of the patient. However, the strap 18 may be locked over the buttons 17, if necessary, after the intubation of tube 11.

Referring to FIG. 2, there is shown a somewhat different tubing assembly including a similar coupling device 12'. This assembly differs from that of FIG. 1 in having a swivel type fitting 23 and an adapter fitting 24 by which the connection between the endo-tracheal tube 11 and the coupling 12' is established, in lieu of the elbow-fitting 20.

The swivel type fitting 23 comprises two parts 25 and 26 having a rotary sealed connection. Part 25 has a slightly tapered sleeve 27 which fits telescopically within the end of the passage 14' in the coupling 12'. Part 26 has a cylindrical recess in which one end of the adapter 24 seats, the other end of the adapter seating telescopically within the tube 11. The adapter also has a collar 28 interposed axially between the end portions thereof which are of different diameter respectively.

The part 25 of the swivel fitting is provided externally with a mushroom-like button 29, and part 26 has a pair of external diametrically opposed mushroom-like buttons 30, all of the buttons being similar to the buttons 17 on the coupling 12.

As will be seen from FIG. 2, an elastic strap 38 is installed between part 25 of the swivel fitting 23 and the coupling 12', a hole 19' midway of the ends of the strap expanding over button 29 and conveniently located holes 19' in the opposite end portion of the strap expanding over the opposite buttons 17' on the sleeve of the coupling 12'. In this assembly the adapter 24 is secured in the part 26 of the swivel fitting by an elastic strap 18', a central hole 19' expanding over one end of the adapter up to collar 28, and holes 19' in opposite end portions of the strap expanding over opposite buttons 30 on part 26.

Referring to FIG. 5, a coupling device 12'' having a modified form of sleeve 13'' is provided. Sleeve 13'' differs from sleeve 13 in having an axial mid portion 31 of larger diameter than the end portions and from which the pair of buttons 17'' project. Also the wall of the sleeve 13'' at the mid portion 31 contains an elongated opening or slot 32.

The slot 32 in sleeve 13'' serves to provide an exhalation port via which air exhaled by the patient may flow directly and unrestrictedly to atmosphere without flowing back to the inhalation valve in the controlled air supply channel.

Installation of the coupling device 12'' is accomplished in a manner similar to that previously described for coupling device 12, utilizing an elastic strap 18'' to elastically hold the elbow fitting 20'' in sealed relation within the coupling sleeve 13''.

While specific forms of coupling devices have been shown and described herein, it will be apparent that variations therein may be made, as well as in the situation in which they may be used, within the scope of the appended claims.

I claim:

1. A coupling assembly for coupling sections of tubing, comprising a sleeve member to the opposite ends of which sections of tubing may be telescopically joined to form a connection, fastening members on opposite sides of said sleeve member, a swivel fitting provided between one of said sections of tubing and said sleeve member, a first elongated resilient strap the opposite ends of which are provided with a plurality of spaced engaging means removably securable to the fastening members on said sleeve member said resilient strap removably engaged intermediate said ends to one part of said swivel fitting, and a second resilient strap removably secured adjacent its opposite ends to fastening members on another part of said swivel fitting and engaged intermediate its said ends to said one section of tubing.

* * * * *